United States Patent [19]

Klein et al.

[11] 4,011,866

[45] Mar. 15, 1977

[54] ELECTRONICALLY CONTROLLED PULMONARY VENTILATOR

[75] Inventors: Fritz F. Klein, Hudson, N.H.; Oliver C. Morse, III, Berkeley, Calif.

[73] Assignee: Automatic Breathing Apparatus Co., Inc., Boston, Mass.

[22] Filed: Aug. 26, 1968

[21] Appl. No.: 767,016

Related U.S. Application Data

[63] Continuation of Ser. No. 430,602, Feb. 5, 1965, abandoned.

[52] U.S. Cl. ............................ 128/145.8; 128/142.3
[51] Int. Cl.² .......................................... A62B 7/02
[58] Field of Search ...................... 128/28, 30, 30.2, 145.5–145.8

[56] References Cited

UNITED STATES PATENTS

| | | | |
|---|---|---|---|
| 2,780,222 | 2/1957 | Polzin et al. | 128/30.2 |
| 2,830,580 | 4/1958 | Saklad et al. | 128/145.8 |
| 3,033,195 | 5/1962 | Gilroy et al. | 128/145.8 |
| 3,101,708 | 8/1963 | Perry et al. | 128/145.5 |
| 3,191,595 | 6/1965 | Wilson | 128/145.5 |
| 3,266,488 | 8/1966 | Andreasen | 128/145.5 |

OTHER PUBLICATIONS

Miller, B. J., *Surgery*, Oct. 1957, vol. 42, No. 4, pp. 722–725.
Rochford et al., *British Journal of Anesthesia*, 1958, 30, 23, pp. 23–31.

*Primary Examiner*—Kyle L. Howell
*Attorney, Agent, or Firm*—Walter J. Kreske

[57] ABSTRACT

Apparatus for effecting automatic inhalation and exhalation by human or animal recipients of air and/or other gases through a tube from a constant pressure gas reservoir by providing in the tube a venting solenoid valve close to the recipient and controlled by an astable multivibrator timer for opening and closing the valve in accordance with the recipient's breathing time schedule, the time being located remotely to the valve and in convenient monitoring relation to an attendant.

8 Claims, 3 Drawing Figures

INVENTORS.
FRITZ F. KLEIN, &
OLIVER C. MORSE III
BY Walter J. Kreske

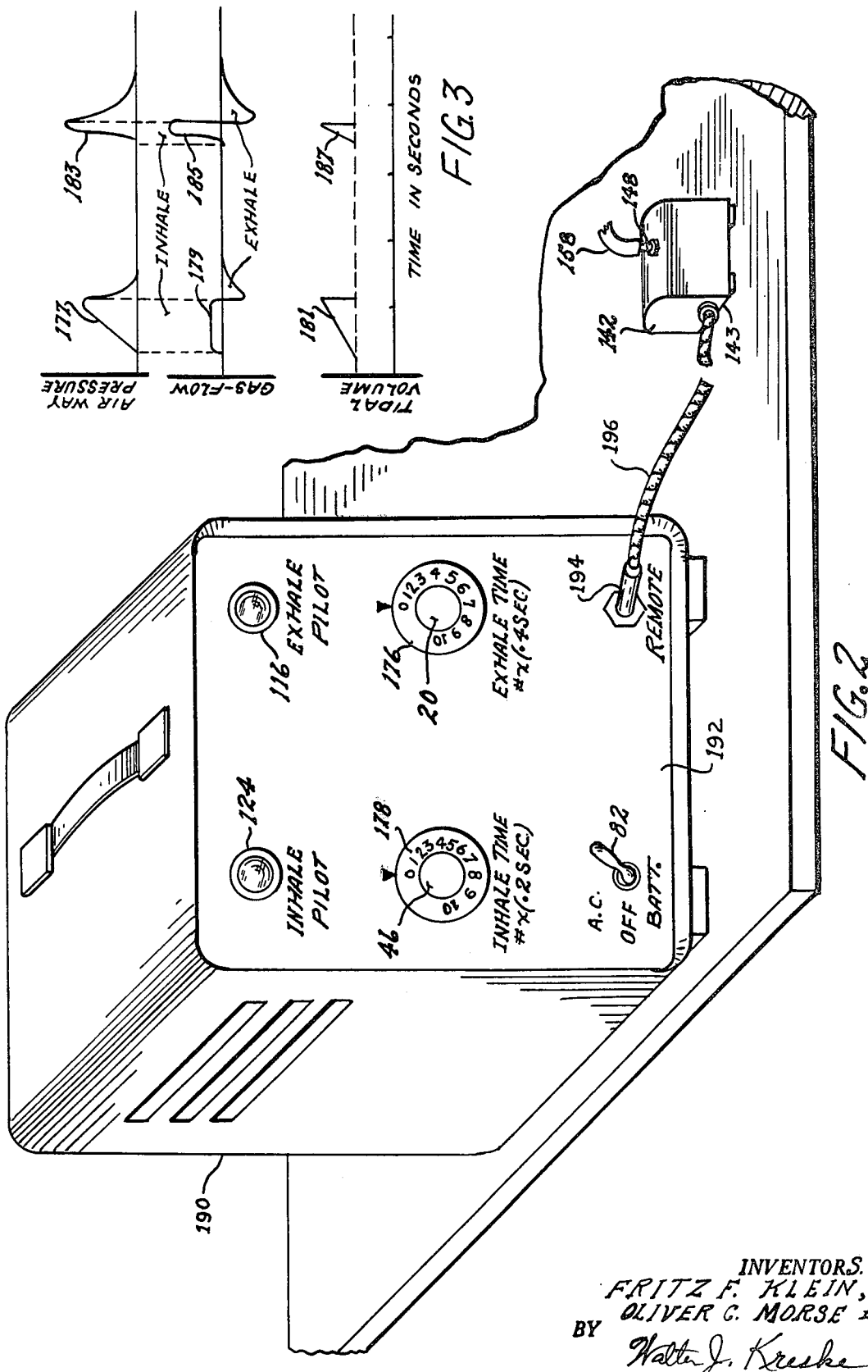

ELECTRONICALLY CONTROLLED PULMONARY VENTILATOR

This is a continuation of application Ser. No. 430,602, filed Feb. 5, 1965, now abandoned.

This invention relates to automatic breathing apparatus, herein termed pulmonary ventilators, and more particularly to apparatus for effecting automatic inhalation and exhalation of air and/or other gases by lung type animals and humans wherein the period of inhalation and exhalation may be independently varied.

In physiological experimentation, surgical anesthesia as well as sustenance of life through proper breathing, it becomes desirable to have reliable apparatus which may automatically force air or other desired gases into the lungs, and particularly an apparatus which may have the inhalation and exhalation time periods independently adjustable so as to adapt to the normal period of such activity by the patient or vary the time and frequency to achieve a desired end result in an experiment or life saving effort. Existing devices attempting to perform this function are in general relatively complex and expensive as well as of a size and configuration which is cumbersome to use.

These problems have been overcome by the present invention of a pulmonary ventilator which also incorporates other desirable features and advantages. Among these other desirable features and advantages of the present invention is that of extreme reliability, ease and simplicity of operation as well as a high degree of compactness for ready hand portability of the apparatus. Another desirable feature is that of the device having a master control unit with capability of operating a remotely located breathing control valve responsive to the master control unit with the remotely located breathing control valve meeting the safety requirements necessary in explosive and inflammable areas such as use with anesthetics in hospital operating rooms. A further desirable feature is that of the apparatus having a low internal compression volume, thus avoiding significant compression of the gas within the ventilator when a patient has a high resistance to inflation. Another desirable feature is that of having a tidal volume characteristic determined by adjusting duration of closure of a breathing control valve or by altering the flow rate of gases from a gas source or reservoir.

A primary object of the present invention is the provision of an automatically controlled pulmonary ventilator for effecting automatic inhalation and exhalation of air or other gas by lung type animals and humans wherein the period of inhalation and exhalation may be independently controlled.

Another object is the provision of a pulmonary ventilator particularly adaptable to the specific characteristics of respiration of premature and full term neonates as well as infants and small animals.

A further object is the provision of a pulmonary ventilator having low internal compression volume.

A still further object is the provision of a pulmonary ventilator having a time cycled tidal volume determined by duration of a breathing control valve closure or flow rate of gases from a gas source or reservoir.

And a still further object is the provision of a pulmonary ventilator which is safe for use in the presence of explosive or flammable agents such as anesthetic gases encountered in hospital operating rooms.

Other objects include the provision of a pulmonary ventilator which is relatively simple to adjust and operate, extremely reliable in operation, relatively small, compact and rugged in construction, light in weight, hand portable, relatively inexpensive to manufacture and is operable at very low electrical power voltages.

These objects, features and advantages are achieved generally by the provision of a pulmonary ventilator for use with an air or other gas reservoir having an outlet at a preselected pressure, comprising a gas flow duct with three gas flow channels communicating therewith, one of the channels being adapted for coupling to the outlet of the gas reservoir, a second channel adapted for coupling to a lung inlet or trachea of a recipient, and the third channel coupled to a relay operated breathing control valve, the relay of the breathing control valve being coupled to an electronic timer control unit for alternate opening and closing of the breathing control valve in accordance with a selected time schedule.

By making the electronic timer unit in the form of an astable multivibrator, a relatively simple, compact and reliable operating arrangement is thereby achieved.

By making the astable multivibrator with a pair of current valves, each associated with a resistor capacitor adjustable charging network as the timing arrangement, relatively simple and accurate preselection and variation of both the closed and open time periods of the breathing control valve as separate entities is thereby achieved.

By providing a driver circuit for driving the relay of the breathing control valve, and arranged to be turned on and off by one of the adjustable resistor capacitor timing networks, accuracy of timing and increased range of timer adjustment of the astable multivibrator is thereby achieved.

By making the relay operated breathing control valve as a separate hand portable assembly remote to the electronic timer unit, versatility and ease of use as well as adaptability to corrosive atmospheres and cramped use quarters is thereby achieved.

By making the relay operable with its assembly at low voltages and currents, safe operation in even explosive atmospheres is thereby achieved.

By coupling a green and a red indicator lamps to the low voltage source and providing a pair of switching contacts in operative relation to the breathing control valve relay, a relatively simple and effective visual indication of inhale and exhale duration and cycling is thereby achieved.

By providing a power transistor circuit as the relay driver and making the astable multivibrator current valves in the form of solid state devices such as transistors, desirable compactness, operating efficiency, reliability and long operating life even on battery power are thereby achieved.

These features, objects and advantages will be better understood from the following description taken in connection with the accompanying drawings of a preferred embodiment of the invention and wherein:

FIG. 2 is an isometric view of the FIG. 1 embodiment circuits in a practical operating arrangement;

FIG. 3 is a graph to more clearly illustrate operation of the FIG. 1 embodiment.

Figure 1:
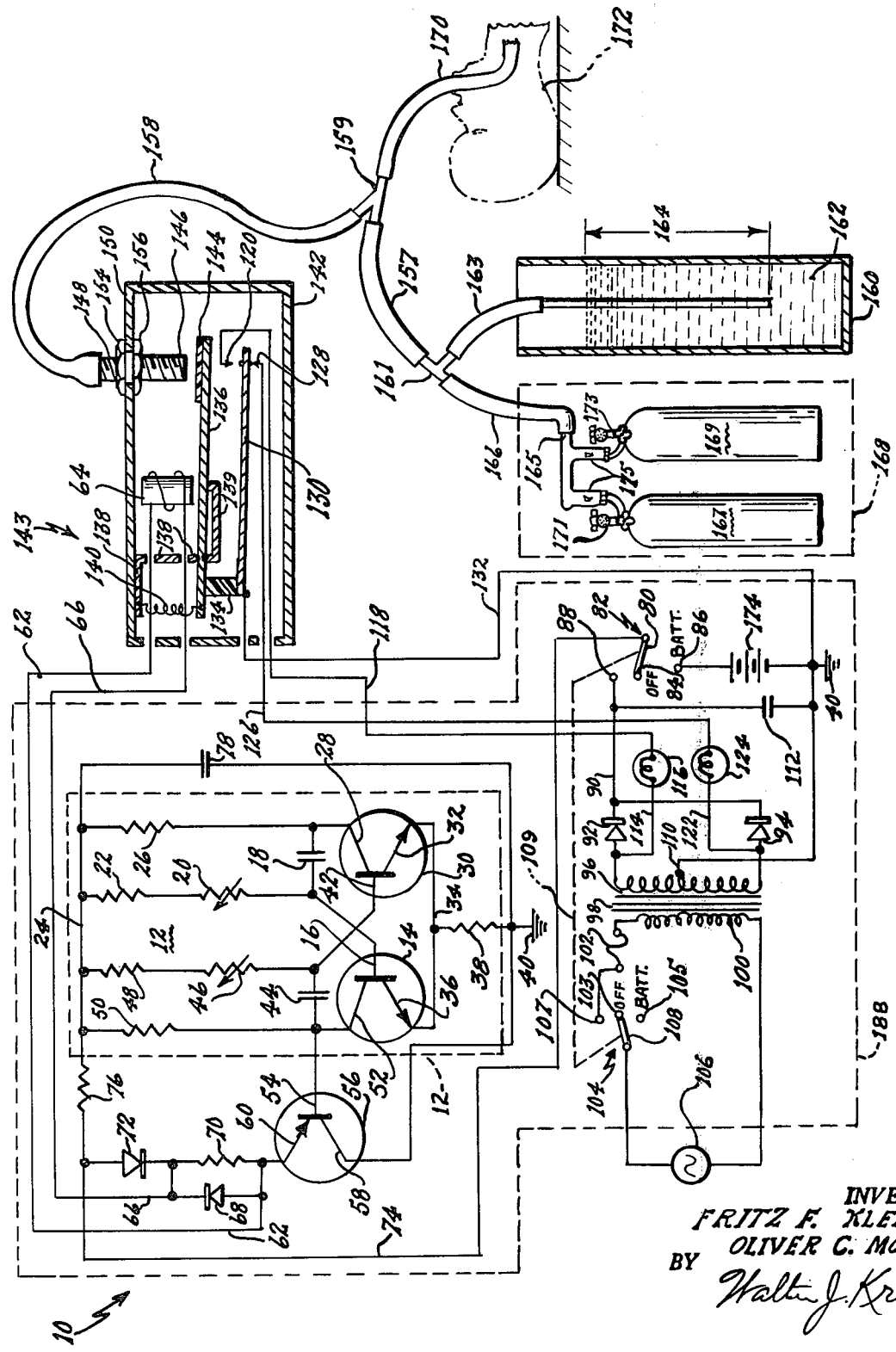
FIG. 1 is a schematic diagram of a preferred embodiment of the invention.

Referring to FIG. 1 in more detail, a pulmonary ventilator in accordance with the present invention is designated generally by the numeral 10. The pulmonary ventilator 10 has an astable multivibrator 12. The astable multivibrator 12 has a current valve 14 such as a transistor having a base 16 coupled to one side of an exhale timing capacitor 18 and through a variable exhale timing resistor 20 in series with a fixed exhale timing resistor 22 to a positive potential supply cable 24. The other side of the exhale timing capacitor 18 is coupled through a charging rise time determining resistor 26 to the positive potential supply cable 24. The exhale timing capacitor 18 and exhale rise time determining resistor 26 are also coupled to a collector 28 of a current valve 30 such as a transistor. The transistor 30 has an emitter 32 which is coupled through a cable 34 to an emitter 36 of the transistor 14. The electric cable 34 is coupled through a stabilizing resistor 38 to ground 40.

The transistor 30 has a base 42 coupled to one side of an inhale timing capacitor 44 and through an inhale timing variable resistor 46 and series coupled fixed resistor 48 to the positive potential power cable 24. The other side of the inhale timing capacitor 44 is coupled through an inahle rise time determining resistor 50 to the positive potential power cable 24 and also to a collector 52 of the transistor 14. The collector 52 is also coupled to a base 54 of a breathing control valve relay driver transistor 56 having a collector 58 coupled to ground 40.

The breathing control valve relay driver transistor 56 has an emitter 60 coupled through an electric cable 62 to one side of a breathing control valve relay solenoid 64, the other side of which is coupled through an electric cable 66 and through a reverse voltage spike suppression diode 68 to the collector 60. The electric cable 66 is also coupled through a residual load determining resistor 70 to the emitter 60. The electric cable 66 is also coupled through a base offset voltage reducing diode 72 to a positive potential power cable 74 which is coupled at one end through a ripple suppression or power supply decoupling resistor 76 to the positive potential power cable 24. The positive potential power cable 24 is also coupled through a decoupling capacitor 78 to ground 40. The other end of the positive potential power cable 74 is coupled to a moveable contact arm 80 of a master power switch 82 which includes an OFF terminal 84, a battery terminal 86 and a positive potential rectified current power supply output terminal 88. The power supply output terminal 88 is coupled through a positive potential power cable 90 and rectifiers 92 and 94 to respective ends of a secondary 96 of a power transformer 98 having a primary 100, one side of which is coupled through a fuse 102 and a switch 104 across a conventional 115 volt alternating current power source 106. The switch 104 is part of the master power switch 82 and has a moveable switch arm 108 coupled by a linkage 109 to operate in unison with the moveable contact arm 80. The switch 104 also includes an OFF terminal 103, a battery terminal 105, and an alternating current power terminal 107 for selective engagement by moveable arm 108 when, due to linkage 109, the switch arm 80 engages terminals 84, 86 and 88 respectively.

The secondary 96 has a centertap 110 coupled to ground 40 and thereby combines with rectifiers 92 and 94 for providing full wave rectification of the alternating current supply. The positive potential power cable 90 is coupled through a smoothing capacitor 112 to ground 40 providing thereby at the power terminal 88 a direct current power supply at near constant voltage.

One end of the secondary 96 is also coupled through an electric cable 114, a red inhale indicator lamp 116 and an electric extension cable 118 to an inhale relay contact terminal 120. The other side of the secondary 96 is coupled through an electric cable 122, a green exhale indicator lamp 124 and an electric extension cable 126 to an exhale relay contact terminal 128. The inhale and exhale relay contacts 120 and 128 operate in conjunction with a moveable contact arm 130 coupled through an electric extension cable 132 to ground 40.

The moveable contact arm 130 is fixed to an insulator support 134 carried by a breathing control valve relay armature 136 fulcrumed to pivot at a support 138 and yieldably held at one end by a tension spring 140 anchored to the support 138 which is fixed to a housing 142 of a remotely located breathing control valve assembly 143. The other end of the breathing control valve relay arm 136 carries a resilient closure pad 144, such as of rubber, positioned to provide an effective gas tight seal at an open end 146 of an exhale nipple 148 preferably threaded about its periphery and extending through an opening in a wall 150 of the remotely located breathing control valve assembly housing 142. The exhale nipple 148 is fixed in place at the housing wall 150 by nuts 154 and 156 adjustably with respect to the resilient pad 144 to insure not only positive sealing of the end 146 by the resilient pad 144 when moved by activation of the solenoid 164, but also proper sequential engagement of the relay inhale contact 120 and exhalation contact 128 respectively when the armature 136 moves upwardly to close the end 146 of nipple 148 and downwardly to open end 146 of nipple 148 as will be hereinafter further described.

The other end of the nipple 148 is coupled through a flexible exhale tube 158 to one leg of a connector 159. Another leg of the connector 159 is coupled through a flexible gas supply tube 157, a second connector 161 and a pressure relief tube 163 to a safety pressure release arrangement which may consist of a container 160 carrying therein water 162 to a level 164 above the open end of pressure relief tube 163 to form a relief channel effecting a preselected maximum operating pressure above which leakage through pressure relief tube 163 and water 162 will occur.

A gas supply channel is formed by another flexible tube 166 coupled at one end to the connector 161 and at the other end to an outlet 165 of a suitable air or other gas reservoir 168. The gas reservoir 168 is preferably comprised of supply tanks 167 and 169 of air, oxygen, anesthetic or other desired gases and have outlet valve and pressure regulators 171 and 173 coupled through gas flow meters 175 to the supply tube 166.

A breathing channel 170 is also formed by a flexible tube coupled at one end to the connector 159 and the other end adapted to be coupled as by insertion in the trachea of a patient or other recipient 172.

In the operation of the pulmonary ventilator 10, gas at a suitable pressure set at the valve and regulators 171 and 173 is maintained from the reservoir 168 at the supply tube 166. Such pressure is normally set below that determined by the height 164 of the safety pressure release arrangement to minimize leakage and loss through exhaust tube 163. The master power control switch 82 has its moveable contact arm 80 moved to the power terminal 88 and thereby the moveable contact arm 108 to the alternating current terminal 107. Thus current from the alternating current power source 106 is fed through the power transformer 98 to produce a positive potential through power line 74 to the astable multivibrator 12 which thereupon makes the transistors 14 and 30 become alternately conductive for predetermined periods set as desired on the adjustable exhale timing resistor 20 and the inhale timing resistor 46 respectively.

In the present instance, by way of example, the exhale timing resistor 20 together with the exhale timing capacitor 18 and fixed resistor 22 are selected to give a variable exhale time period range from 0.4 to 4 seconds. In similar manner, the inhale timing variable resistor 46, fixed resistor 48 and inhale timing capacitor 44 are selected to give an inhale time period adjustable between 0.2 and 2 seconds. While these time periods for operation of the astable multivibrator 12 have been found particularly suitable for neonates and infants, it should be noted that such operating time periods may be varied to suit a particular use condition by changing either the timing resistors or timing capacitors or both.

When the multivibrator transistor 14 becomes conductive, current flows from the positive power cable 24 through the inhale rise time resistor 50, collector 52, emitter 36 and stabilizing resistor 38 to ground 40. This current flow places the potential at collector 52 at substantially ground potential, thereby placing the base 54 of the breathing control valve relay driver transistor 56 at substantially the same ground potential and thus causes the breathing control valve relay driver transistor 56 to become conductive. Conduction in the driver transistor 56 causes current flow from the positive power cable 74 through the base offset voltage reducing diode 72 and the electric cable 66, relay solenoid 64, electric cable 62 to the emitter 60 of the relay valve driver transistor 56, thereby energizing the relay solenoid 64 and causing the breathing control valve relay armature 136 to carry the resilient pad 144 against the open end 146 of the exhale nipple 148. Thereby the preset gas pressure builds up through the supply channel 166 and appears through the breathing channel 170 in the trachea of the patient 172 causing an inhalation gas flow and tidal volume to the lungs of the patient 172. The resulting airway pressure, gas flow and tidal volume during this inhalation period set on the inhale adjustable timing resistor 46 as explained above is represented in FIG. 3 by curves 177, 179 and 181 respectively for longer period low flow rates and by curves 183, 185 and 187 respectively for short period high flow rates.

After this period of inhalation, when the inhalation timing capacitor has dissipated its charge, the transistor 30 is then fired and transistor 14 becomes non-conductive. Non-conduction in transistor 14 thereby de-energizes the breathing control valve relay solenoid 64 which permits gravity and the spring 140 to cause the armature 136 to move downwardly and open the end 146 of the exhale nipple 148. Thereby, the pressure in the exhale tube 148 drops, causing the pressure in the lungs of the patient 172 to exhaust and fall to the room pressure at the opening 146 as shown in the graph of FIG. 3. Such exhale period will continue for the length of time set upon the adjustable exhale resistor 20 as explained above. This alternate inhaling and exhaling operation will continue so long as the power switch 82 is in the position described above.

In the event power from the source 106 fails, or it is desired to operate without the power source 106, the master power switch 82 may have its contact arm 80 moved from the terminal 88 down through the OFF position 84 to the battery terminal 86, thereby coupling a battery 174 to the positive power cable 74 to cause operation of the device as explained above with respect to the alternating current source 106.

During the continuous operation of the breathing control valve relay armature 136, each time the armature 136 is pulled upwardly by the relay solenoid 64 to close the end 146 of the nipple 148, the contact arm 130 likewise moves upwardly to engage the inhale terminal 120 thereby completing the circuit through the red inhale indicator lamp 116 causing it to light and indicate the inhale or inspiration period (FIG. 3). When the breathing control valve relay armature 136 is pulled downwardly by gravity and the spring 140, it causes the moveable contact arm 130 to also move downwardly against the exhale relay terminal 128 so as to complete the circuit to the green exhale indicator lamp 124 causing it to light and indicate the exhale period (FIG. 3).

The inhale lamp 116 and exhale lamp 124 are thereby in synchronism with the inhale and exhale functions hereabove described and provide a direct visual indication and check on proper pulmonary ventilator operation both as to time and duration of each inhale and exhale period as set on the calibrated dials 176 and 178 (FIG. 2) which accompany the adjusting knob of the working embodiment of the exhale timing resistor 20 and inhale timing resistor 46 respectively. As a further convenience, the exhale timing resistor 20 is selected with a value such that the exhale time period is indicated by the number setting on the dial 176 multiplied by 0.4 and the inhale timing resistor 46 is selected with a resistive value such that the inhale time period is indicated by the number setting on the dial 178 multiplied by 0.2 which permit a maximum exhale period setting of 4 seconds and a maximum inhale period of 2 seconds. These ranges of adjustment of exhale and inhale time periods separately have been found sufficient to accomodate both those cases where a high gas flow of short duration is desirable and where low flow of longer duration is desired as shown in curves 185 and 179 in FIG. 3. It also permits a desirable wide range of exhale time period adjustment to accomodate even patients with prolonged pulmonary emptying and thereby insuring complete expiration before each subsequent inhale cycle.

It will be noted by inspection of FIG. 1 that the relative short length and small diameter of the airway tubes 157, 158, 166, 163, 170, connectors 159, 161 and exhaust valve nipple 148 provide only a relatively small airway volume so that when the pad 144 closes the end 146 of the nipple 148 causing buildup of pressure in the airways from the gas reservoir 168, the internal compression volume of the airways will still be relatively low. Thus there will be a rapid response of airway pressure to respective openings and closings of the end 146 of nipple 148 by the pad 144 to thereby properly accomodate rapid breathing rates and small lung capacities of neonates, infants and small animals. It will be noted also that the valve assembly 143, being independently moveable with respect to the control structure 188 may be placed close to the patient 172 to thereby further shorten airway tube 158 to further minimize airway volume and desirably enhance the low compression volume characteristic of the airways. It will further be noted that even when the nipple 148 is open in the exhale period of the patient 172, fresh gas from the gas reservoir 168 continues to flow through the airway tubes 166, 161, 157, 159, 158 and nipple 148, thereby continually purging stale exhaled air from the patient 172 and confining dead space to only the short, low volumetric catheter 170 which is much smaller than the lung capacity of the patient 172 so that dangerous, negative pressures are not needed for reducing dead space.

Particular convenience and versatility is achieved by mounting the power supply and electronic timer control structure 188 in a separate hand portable housing 190 (FIG. 2) with a front panel 192 carrying in manually accessible and simultaneously visible position the operating lever of the master switch 82, green exhale indicator light 116, red inhale indicator light 124, the manual adjusting knobs of the variable exhale resistor 20 and variable inhale resistor 46. The panel 192 also carries a multi terminal jack 194 with a chord 196 carrying the electric extension cables 62, 66, 118, 126 and 132 to the remotely located breathing control valve assembly 143. In the present instance the power terminals 86 and 88 carry only 7½ volt direct current potential for operation of the breathing control valve assembly 143 to permit safe operation with flamable gases.

This invention is not limited to the particular details of construction and operation described as equivalents will suggest themselves to those skilled in the art.

What is claimed is:

1. In a pulmonary ventilator for use with a reservoir of gas having an outlet at a preselected pressure, the combination of three intercommunicating gas flow channels, one of said gas flow channels adapted for coupling to said outlet of said gas reservoir, another of said gas flow channels adapted for insertion in the trachea of a pulmonary ventilation recipient, a single relay breathing control valve means having a single breathing control valve in said ventilator, the third of said gas flow channels being an exhaust channel coupled to said single breathing control valve of said single relay breathing control valve means for selectively closing and opening said third channel to passage of said gas and thereby respectively applying said preselected pressure gas to said trachea and exhausting said gas through said third channel, and electronic timer control means coupled to the relay of said relay breathing control valve means to cause alternate closing and opening of said single breathing control valve in accordance with a preselected time schedule.

2. The combination as in claim 1 wherein said gas flow channels are tubes having substantially the same diameter as said trachea.

3. In a pulmonary ventilator for use with a reservoir of gas having an outlet at a preselected pressure, the combination of three intercommunicating gas flow channels, one of said gas flow channels adapted for coupling to said outlet of said gas reservoir, another of said gas flow channels adapted for insertion in the trachea of a pulmonary ventilation recipient, a single relay breathing control valve means having a single breathing control valve in said ventilator, said single relay breathing control valve means including means for yieldably maintaining said single valve open, the third of said gas flow channels being an exhaust channel coupled to said single breathing control valve of said single relay breathing control valve means for selectively closing and opening of said third channel to passage of said gas and thereby respectively applying said preselected pressure gas to said trachea and exhausting said gas through said third channel, and electronic timer control means coupled to the relay of said relay breathing control valve means and including means for energizing said relay for overcoming said yieldable means to cause alternate closing and opening of said single breathing control valve in accordance with a preselected time schedule.

4. The combination as in claim 3 wherein the electronic timer control means includes electric driver means for providing said energizing of said relay to effect said valve closing, and an astable multivibrator for providing said time schedule to said energizing means.

5. The combination as in claim 4 wherein said relay breathing control valve means is readily hand portable independently of said electronic timer control means and in remote relation to said electronic timer control means and adapted for placement close to said recipient during use.

6. The combination as in claim 5 wherein said electronic timer control means is readily hand portable and has capacity for placement in convenient monitoring relation to an attendant.

7. The combination as in claim 6 wherein said electronic timer control means includes two valve operation indicator lamps, means cooperating with said relay breathing control valve means for causing one of said lamps to glow when said control valve is closed and the other to glow when said valve is open, and said astable multivibrator includes a pair of resistive-capacitive timer circuits with the resistors being variable and each resistor carrying a manually accessible adjusting knob with calibrations cooperating with one of said knobs for indicating selectable closed time duration of said valve and calibrations cooperating with the other of said knobs for indicating selectable open time duration of said valve.

8. The combination as in claim 7 wherein the valve closure time duration calibrations are over a scale range equal to one half the valve open time duration calibrations.

* * * * *